United States Patent [19]

Miyano

[11] Patent Number: 5,354,322

[45] Date of Patent: Oct. 11, 1994

[54] OPTICAL ILLUMINATION SYSTEM FOR ENDOSCOPE

[75] Inventor: Hitoshi Miyano, Omiya, Japan

[73] Assignee: Fuji Photo Optical Co., Ltd., Saitame, Japan

[21] Appl. No.: 2,872

[22] Filed: Jan. 19, 1993

[30] Foreign Application Priority Data

Jan. 17, 1992 [JP] Japan .................. 4-001245[U]

[51] Int. Cl.$^5$ ............................... A61B 1/06
[52] U.S. Cl. .......................... 607/88; 128/4; 606/17
[58] Field of Search ............... 128/633-634, 128/664-667, 4, 6; 606/2, 3, 10-11, 17; 607/88-89

[56] References Cited

U.S. PATENT DOCUMENTS 3,494,354 2/1970 Yokota et al. .................. 128/665
4,446,871 5/1984 Imura ............................ 128/664 X
5,167,686 12/1992 Wong ............................. 128/634 X Primary Examiner—Angela D. Sykes
Attorney, Agent, or Firm—Keck, Mahin & Cate

[57] ABSTRACT

An endoscope illumination optical system includes a spherical lens element and a divergent lens element, positioned in order from a circular light exit end of a light guide fiber bundle. The spherical lens element has a refractive index n satisfying the following conditions when $\sin = r/R$:

$$1.8 \cos(\Theta/2) < n < 2.2 \cos(\Theta/2) \text{ and}$$

$$r < R$$

where r is the radius of said light exit end of said light guide fiber bundle; and R is the radius of said transparent spherical element.

7 Claims, 1 Drawing Sheet

OPTICAL ILLUMINATION SYSTEM FOR ENDOSCOPE

BACKGROUND OF THE INVENTION

1. Field of the Invention

This invention relates to an optical system for an endoscope for providing divergent rays of light from an illumination light guide so as to illuminate a wide field of view of the endoscope.

2. Description of Related Art

Typically, endoscopes or fiberscopes have an image guide fiber bundle and a light guide fiber bundle both of which are in a flexible, elongated sheath or tube. In order to view or photograph an object through the image guide fiber bundle, the endoscope handled with the forward end of the light guide fiber bundle directed closely to the object so as to illuminate the object.

One recent design demand for such an endoscope, in particular a medical endoscope, is to reduce the outer diameter of a flexible sheath or tube as small as possible for relieving or not causing pain to the patients while providing ease of observation. In order for the endoscope to satisfy this demand, it is essential to install both the image fiber bundle and the light guide fiber bundle in as thin and compact package as possible. This unavoidably requires the installation of an objective lens having a wide field of view along with an illumination optical system having a wide angle of illumination. Japanese Unexamined Utility Model Publication No. 2-140519 reveals one technique for widening an angle of illumination of the illumination optical system of the endoscope. As shown in FIG. 2, a wide angle illumination optical system, as described in the above mentioned publication, includes a plurality of lenses, such as a convex lens 12A, a convex lens 12B and a concave lens 13 arranged in order from the fiber bundle side. The first two convex lenses 12A and 12B forms a convergent lens system functioning to gather illumination light emanating from the light guide fiber bundle 11 and focus it at a point. The concave lens 13, which is a divergent lens, functions to diverge the illumination light.

However, to provide the prior art illumination optical system with a sufficiently wide divergent angle covering a sufficiently wide field of view of an objective lens practically requires more than two convex lenses. Any increase in the number of optical elements included necessary results in an increase in manufacturing cost of the endoscope, and such is undesired.

SUMMARY OF THE INVENTION

It is therefore an object of the present invention to provide an illumination optical system for endoscopes which includes only a small number of optical elements and yet achieves a wide field of illumination.

The foregoing object of the present invention is accomplished by providing an illumination optical system for an endoscope having a light guide fiber bundle, received in an elongated sheath or tube, for emitting light rays in parallel with its optical axis. The illumination optical system includes a transparent spherical optical element, such as a spherical optical lens. Light rays emitting from a circular light exit end of the light guide fiber bundle, which are in parallel with the optical axis of the light guide fiber bundle, are focused once on a preselected point on the spherical surface of the spherical optical element by the action of the spherical optical element, and thereafter, the rays are diverged so as to illuminate a wide view field of an image guide system.

The illumination optical system includes a divergent optical element, such as a plano-concave lens and a Fresnel lens, arranged after the spherical optical element with respect to the light guide fiber bundle. Providing the divergent optical element enables the illumination optical system to illuminate a greatly widened area sufficiently covering a wide view field of an image guide system.

The transparent spherical element, whose center is positioned on the optical axis of the light guide fiber bundle, has a refractive index n satisfying the following conditions when $\sin \Theta = r/R$:

$$1.8 \cos (\Theta/2) < n < 2.2 \cos (\Theta/2) \text{ and}$$

$$r < R$$

where r is the radius of said light exit end of said light guide fiber bundle; and R is the radius of said transparent spherical element.

Since the illumination optical system is structured to contain only one optical element, i.e. a single spherical optical lens, positioned in front of or in contact with a light exit end of the light guide fiber bundle, the number of optical elements of the illumination optical system is considerably reduced compared to that of conventional known ones. This results in a decrease in manufacturing steps.

Providing the divergent optical element, such as a plano-concave lens, positioned after the spherical optical element considerably widens the field of illumination of the illumination optical system, so as to sufficiently cover a widened view field of the image guide system.

When the spherical optical element has a refractive index as defined above, light rays emitting from the light guide fiber bundle focus on a predetermined or preselected point on the spherical surface of the spherical optical element where the optical axis of the light guide fiber bundle intersects. Consequently, the light rays, after having passed through the spherical optical element, are effectively diverged.

BRIEF DESCRIPTION OF THE DRAWINGS

The above and other objects and features of the present invention will be clearly understood from the following detailed description with respect to preferred embodiments thereof when considered in conjunction with the accompanying drawings, in which.

DETAILED DESCRIPTION OF THE PREFERRED EMBODIMENT

Because endoscopes are well known in structure and operation, the present description will be directed in particular to elements forming part of, or cooperating directly with, an illumination optical system in accordance with the present invention. It is to be understood that parts or elements which are not of direct importance to the invention and parts or elements which are purely of conventional constructions will not be described in detail and that parts or elements not specifically shown or described can take various forms well known to those skilled in the optical art.

Figure 1:
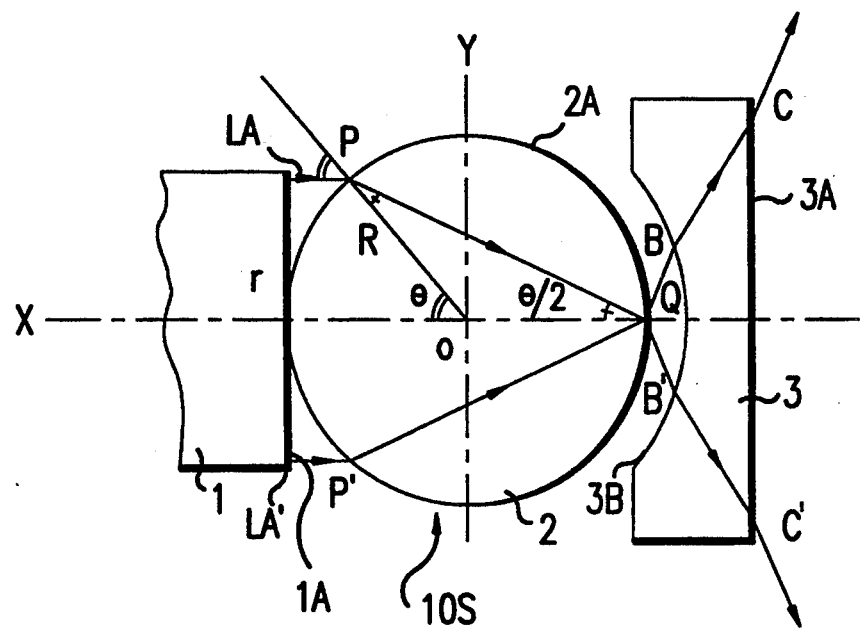
FIG. 1 is a schematic illumination optical system for an endoscope in accordance with a preferred embodiment of the present invention.
Figure 2:
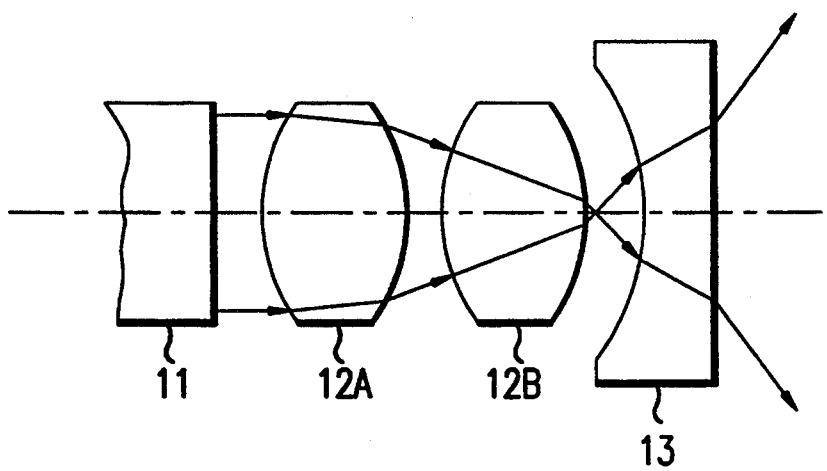
FIG. 2 is a schematic illumination optical system for a prior art endoscope.

Referring to the drawings in detail, and in particular, to FIG. 1, an optical illumination system IOS for an endoscope in accordance with a preferred embodiment of the present invention is shown, comprising a flexible light guide fiber bundle 1 having a circular exit end surface 1A. The illumination system IOS further includes a convergent optical element, such as a spherical optical element or lens 2 externally contacting with the circular exit end surface 1A of the fiber bundle 1, and a divergent optical element, such as a plano-concave lens 3. The plano-concave lens 3, concave to the spherical lens 2, is positioned with an air space relative to or from the spherical lens 2. The spherical lens 2 is made of optically uniform glass materials, or otherwise of optically uniform transparent plastics. The spherical lens 2 and the concave lens 3 are coaxially aligned with the optical axis X and are built within a forward end portion of a flexible, elongated sheath or tube (not shown). The plano-surface 3A of the plano-concave lens 3 serves as a barrier surface of the illumination optical system IOS.

The spherical lens 2 is designed as a convergent lens element so as to converge the rays of illumination light once and then diverge them for providing the illumination optical system IOS with high luminous exitance. When $\sin \Theta = r/R$ ($r < R$), the theoretical refractive index n of the spherical lens 2 is defined by the following equation (I):

$$n = 2 \cos (\Theta/2) \qquad (I)$$

where r is the radius of the circular exit end surface 1A; and
R is the diameter of the spherical lens 2.

When the equation (I) is satisfied, the parallel pencil of rays of illumination light, emitting from the circular exit end surface 1A of the fiber bundle 1 and entering into the spherical lens 2, converges at a point Q where the optical axis X intersects the spherical surface 2A of the spherical lens 2 at a point remote from bundle/and near to the concave surface 3B of the plano-concave lens 3. Specifically, if the outermost ray of illumination light LA or LA' emitting in parallel with the optical axis X from the circular exit end surface 1A of the fiber bundle 1 enters into the spherical lens 2, with its center O placed in the optical axis X, at a point P on the spherical surface 2A of the spherical lens 2, the angle $\Theta$ is given by the following equation (II):

$$\Theta = \sin^{-1} (r/R) \qquad (II)$$

Describing mathematically, in order that the parallel pencil of rays of illumination light, emitting from the circular exit end surface 1A of the fiber bundle 1, converge or focus on the spherical surface 2A at the point Q in the optical axis X, the outermost light ray LA or LA, must reach the point Q. Since the triangle OPQ is an isosceles triangle, the angle OPQ is equal to the angle OQP, which is $\Theta/2$, and the angle between lines OP and AP is $\Theta$, and the following equation (III) holds from the law of refraction:

$$\sin \Theta = n \sin (\Theta/2) \qquad (III)$$

This equation may be changed as follows:

$$n = \sin \Theta / \sin (\Theta/2) \qquad (IV)$$

On the other hand, it is apparent that the following equation (V) geometrically holds:

$$\sin \Theta = \sin 2 (\Theta/2) = 2 \sin (\Theta/2) \cos (\Theta/2) \qquad (V)$$

After all, by substituting the equation (V) into the equation (IV), the equation (I) is obtained.

Accordingly, as long as the spherical lens 2 satisfies the condition (I) and light rays, emanating from the circular exit end surface 1A of the light guide fiber bundle 1, are in parallel with the axis X, the light rays focus at the point Q all together.

In this instance, it is not always required for the spherical lens 2 to strictly have the theoretical refractive index defined by the equation (I) but it is sufficient if it is close to the theoretical refractive index. However, if the refraction of the spherical lens 2 is excessively small, the point Q, at which parallel rays emanating from the circular exit end surface 1A of the light guide fiber bundle 1, becomes far away from the concave surface 3B of the plane-concave lens 3, so that the plane-concave lens 3 diverges the light rays at a small angle of illumination. This results in increasing the field of illumination insufficiently to cover the field of view of the objective lens of the endoscope. On the other hand, if the refraction of the spherical lens 2 is excessively great, the point Q becomes too close to the concave surface 3B of the plane-concave lens 3 to diverge the light rays so as to appropriately cover the field of view of the objective lens of the endoscope- As a result, the field of illumination is widened in excess, and the illuminance of an object is reduced.

On the basis of a great deal of practical experience of the inventor of this application, limits of deviation of a practical refractive index n of the spherical lens 2 are determined to be approximately 20% of the theoretical value. That is, the practical refractive index the spherical lens 2 must have is defined as follows:

$$1.8 \cos (\Theta/2) < n < 2.2 \cos (\Theta/2)$$

In the manner as described above, the light rays, emanating from the spherical lens 2 at the point Q, enters into the plano-concave lens 3 within a circular extremity, which is indicated by diametrical opposite points B and B', and exit therefrom within a circular extremity, which is indicated by diametrical opposite points C and C', to be diverged widely. Although the outer surface of the objective lens system, exposing the outside area surrounding of the endoscope, is easily soiled or darted by, for instance, the residue within the stomach of a patient, the plano-surface of the plano-concave lens 3 makes it quite easy to wash and clean off the soil or dart.

It is to be understood that the plano-concave lens 3 may be replaced for the divergent optical element with a Fresnel lens designed so as to diverge light rays uniformly within a desired field of illumination.

It is also to be understood that although the present invention has been described in detail with respect to a preferred embodiment thereof, various other embodiments and variants may occur to those skilled in the art. Such other embodiments and variants fall within the scope and spirit of the invention and are intended to be covered by the following claims.

What is claimed is:

1. An illumination optical system for an endoscope, comprising:
    a sheath;
    a light guide fiber bundle, received in said sheath and having a circular light exit end, for emitting light rays in parallel with its optical axis;
    a transparent spherical element, positioned adjacent said circular light exit end of said light guide fiber bundle, for focusing said light rays on a preselected point on the surface of the spherical element remote from said circular light exit end of said light guide fiber bundle; and
    mounting means for mounting said bundle and spherical element with a center of the spherical element lying on the optical axis of the bundle.

2. An illumination optical system as defined in claim 1, and further comprising a divergent optical element, mounted in said mounting means remote from said light guide fiber bundle with respect to said transparent spherical element, for diverging light rays exiting from said transparent spherical element.

3. An illumination optical system as defined in claim 2, wherein said divergent optical element comprises a plano-concave lens presenting its concave side to said transparent spherical element.

4. An illumination optical system as defined in claim 2, wherein said divergent optical element comprises a Fresnel lens.

5. An illumination optical system as defined in claim 2, wherein said transparent spherical element has a refractive index n satisfying the conditions (a) $\sin \Theta = r/R$:

$$1.8 \cos (\Theta/2) < n < 2.2 \cos (\Theta/2) \text{ and}$$

$$(b) r < R$$

where r is the radius of said light exit end of said light guide fiber bundle; and
    R is the radius of said transparent spherical element.

6. An illumination optical system as defined in claim 5, wherein said transparent spherical element is composed of optical glass.

7. An illumination optical system as defined in claim 5, wherein said transparent spherical element is composed of optical plastic.

* * * * *